(12) United States Patent
Arulmoli et al.

(10) Patent No.: US 8,129,536 B2
(45) Date of Patent: Mar. 6, 2012

(54) METHOD FOR THE PURIFICATION OF LANSOPRAZOLE

(75) Inventors: Thangavel Arulmoli, Tamil Nadu (IN); Siripragada Mahender Rao, Tamil Nadu (IN); Krishna Sumanth Peraka, Dublin (IE); Ariyamuthu Sundara Selvan, Tamil Nadu (IN)

(73) Assignee: Orchid Chemicals & Pharmaceuticals Limited, Tamil Nadu (IN)

( * ) Notice: Subject to any disclaimer, the term of this patent is extended or adjusted under 35 U.S.C. 154(b) by 366 days.

(21) Appl. No.: 12/311,220

(22) PCT Filed: Sep. 21, 2007

(86) PCT No.: PCT/IB2007/002734
§ 371 (c)(1),
(2), (4) Date: Jun. 11, 2009

(87) PCT Pub. No.: WO2008/035189
PCT Pub. Date: Mar. 27, 2008

(65) Prior Publication Data
US 2010/0010230 A1     Jan. 14, 2010

(30) Foreign Application Priority Data
Sep. 22, 2006 (IN) ............... 1736/CHE/2006
Dec. 22, 2006 (IN) ............... 2390/CHE/2006

(51) Int. Cl.
*C07D 401/12* (2006.01)

(52) U.S. Cl. .................................... 546/273.7

(58) Field of Classification Search ............... 546/273.7
See application file for complete search history.

(56) References Cited

U.S. PATENT DOCUMENTS

| 4,628,098 A | 12/1986 | Nohara et al. |
| 5,578,732 A | 11/1996 | Kato et al. |
| 6,002,011 A | 12/1999 | Kato et al. |
| 6,180,652 B1 | 1/2001 | Tsujii et al. |
| 6,909,004 B2 | 6/2005 | Singer et al. |
| 7,022,859 B2 | 4/2006 | Singer et al. |
| 7,060,837 B2 | 6/2006 | Singer et al. |

FOREIGN PATENT DOCUMENTS

| WO | WO 2004/018454 A1 | 3/2004 |
| WO | WO 2006/074952 A1 | 7/2006 |

*Primary Examiner* — Patricia Morris
(74) *Attorney, Agent, or Firm* — Oliff & Berridge, PLC

(57) ABSTRACT

The present invention relates to an improved process for the preparation of Lansoprazole of formula (I). More particularly, the present invention relates to a method for the purification of crude Lansoprazole in a solvent in presence of an alkali salt of an organic acid or in presence of an organic base such as piperidine or imidazole.

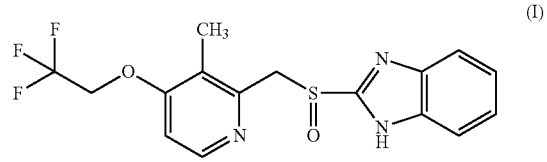

(I)

10 Claims, No Drawings

METHOD FOR THE PURIFICATION OF LANSOPRAZOLE

FIELD OF THE INVENTION

The present invention relates to an improved process for the preparation of Lansoprazole of formula (I). More particularly, the present invention relates to a method for the purification of crude Lansoprazole in a solvent in presence of an alkali salt of an organic acid or in presence of an organic base such as piperidine or imidazole.

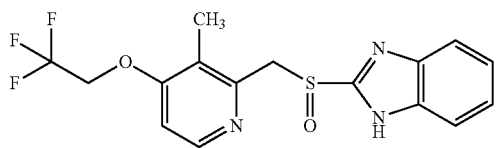

BACKGROUND OF THE INVENTION

Lansoprazole is chemically known as 2-(2-Benzimidazolylsulfinylmethyl)-3-methyl-4-(2,2,2-trifluoroethoxy)pyridine. It is a $H^+/K^+$-ATPase Inhibitor and has the following structural formula:

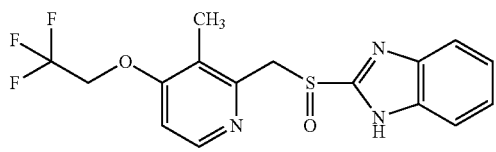

Lansoprazole is specifically known from U.S. Pat. No. 4,628,098. Lansoprazole is an anti-ulcer drug and it is marketed as Prevacid ® by TAP Pharmacetuicals Products Inc.

The preparation of Lansoprazole by conventional methods is always accompanied by the formation of small quantities of the corresponding sulfone derivative as an impurity. For example, U.S. Pat. No. 6,180,652 ("the '652 patent") describes the presence of sulfone derivative. Formation of sulfone derivative brings about the drawback of low yield of the desired sulfoxide. Although attempts have been made to separate the sulfone derivative from Lansoprazole, it is not a simple task, given their very similar structures and physicochemical properties. For this purpose the '652 patent describes a method that permits separation of Lansoprazole from its sulfone derivative and discloses an acetone complex of the Lansoprazole salt.

U.S. Pat. No. 5,578,732 patent describes the crystallization of Lansoprazole using an ethanol:water solvent system.

U.S. Pat. No. 6,002,011 (the '011 patent) describes the crystallization of Lansoprazole from the same ethanol:water system, containing traces of ammonia (0.03 mole $NH_4OH$:1 mole Lansoprazole). The '011 patent discloses a reslurry method in water, which permits to obtain more stable "solvent free" Lansoprazole. The '011 patent fails to disclose the level of purity for Lansoprazole.

U.S. Pat. No. 6,909,004 patent claims a method of purifying Lansoprazole to obtain Lansoprazole having less than about 0.1%, wt/wt, water comprising the steps of: a) providing a solution of Lansoprazole in a solvent selected from an organic solvent (especially ethanol, which is disclosed) or a mixture of organic solvent and water in the presence of an amine compound (ammonia, ammonium hydroxide, diethyl amine, triethyl amine, or methyl amine), wherein the amine compound is present at a ratio of about 1:1, mole:mole, relative to Lansoprazole; b) combining the provided solution with an acid; c) isolating the Lansoprazole; d) dissolving the isolated Lansoprazole in an organic solvent selected from the group consisting of acetone, 2-butanone, methanol, dimethyl-carbonate, and diethyl-carbonate; and e) isolating the purified Lansoprazole having less than about 0.1%, wt/wt, water.

The U.S. Pat. No. 7,060,837 patent claims a method of purifying Lansoprazole, comprising the steps of: a) providing a solution of Lansoprazole in a solvent selected from an organic solvent (acetone, 2-butanone, dimethyl-formamide and tetrahydrofuran, ethanol, methanol, n-propanol, and i-propanol) or a mixture of organic solvent and water in the presence of an amine compound (ammonia, ammonium hydroxide, diethylamine, triethylamine and methylamine); b) combining the provided solution with an acid (acetic acid, formic acid, and hydrochloric acid), and c)isolating the purified Lansoprazole.

The U.S. Pat. No. 7,022,859 patent claims a method of preparing a Lansoprazole containing less than about 0.1% (wt/wt) water, comprising the steps of: a) crystallizing a Lansoprazole from solution in a solvent that is an organic solvent (acetone, 2-butanone, methanol, dimethyl-carbonate, and diethyl-carbonate) or a mixture of an organic solvent and water; and b) isolating the Lansoprazole containing less than about 0.1% (wt/wt) water.

Lansoprazole tends to lose stability and undergo decomposition when contaminated with traces of a solvent particularly water in their crystal structure. It is desirable that the Lansoprazole crystals be solvent free (i.e., residual solvent should be reduced to a minimum).

There is continuing need to obtain Lansoprazole which are free of contaminants including sulfone and sulfide derivatives.

We focused our research to develop an improved and efficient process for the purification of the compound of formula (I) in commercial scale using a solvent in presence of an alkali salt of an organic acid or in presence of an organic base such as piperidine or imidazole.

The disclosed process has advantages of simple operations, higher yield and purity, mild reaction conditions, and is suitable for industrial production over the processes described in the related prior arts.

OBJECT OF THE INVENTION

The main objective of the present invention is to provide a method for the purification of compound of formula (I) in good yield and high chemical purity.

Another objective of the present invention is to provide a method for the purification of compound of formula (I), which would be easy to implement on commercial scale and is economically viable.

SUMMARY OF THE INVENTION

Accordingly, the present invention provides a method for the purification of Lansoprazole of formula (I) having purity more than 99.90%. More particularly, the present invention provides a method for yielding highly purified Lansoprazole of formula (I) in a solvent in presence of an alkali salt of an organic acid or in presence of an organic base such as piperidine or imidazole.

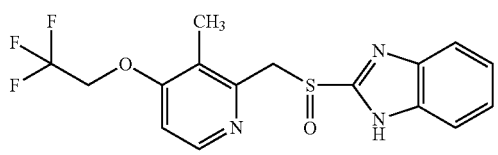

The said process comprising the steps of:
a) dissolving crude Lansoprazole in a solvent in the presence of an alkali salt of an organic acid or an organic base selected from a group consisting of piperidine and imidazole; and
b) isolating pure Lansoprazole.

DESCRIPTION OF THE INVENTION

In an embodiment of the present invention, the purification is preferably performed in a solvent, which is selected from the group comprising of methanol, ethanol, n-propyl alcohol, isopropyl alcohol, n-butanol, isobutanol, tertiary butanol, water and mixtures thereof, most preferably aqueous ethanol.

In another embodiment of the present invention, the purification is preferably performed in using alkali salt of organic acid, which is selected from the group comprising of sodium 2-ethylhexanoate, potassium 2-ethylhexanoate, sodium acetate, potassium acetate, sodium citrate, sodium lactate and the like, most preferably sodium 2-ethylhexanoate.

In an embodiment of the present invention, the purification is preferably performed in using an organic base, which is selected from the group comprising of morpholine, N-methylmorpholine, pyridine, piperidine, imidazole and mixtures thereof.

The use of piperidine, imidazole and alkali metal salt of an organic acid preferably sodium 2-ethylhexanoate in the purification steps brings down the impurity more particularly the sulfone impurity present in the crude Lansoprazole, thereby yielding the Lansoprazole having purity more than 99.90%; apart from the said advantage the present purification yields the final API in good color. Further the purification method described herein has been found to work excellently well even if the sulfone impurity is present in crude Lansoprazole at 3-5% level. The Lansoprazole thus obtained according to the invention described herein is optionally subjected to re-crystallization using acetone or IPE or mixtures thereof.

In yet another embodiment of the present invention, the purification is preferably performed at a temperature in the range of (−) 10° C. to 80° C.; most preferably at a temperature in the range of 20° C. to 60° C.

In the present invention the starting materials were prepared according to the literature available in the prior art.

The present invention is illustrated with the following examples, which should not be construed for limiting the scope of the invention.

EXAMPLE (1)

Purification of Lansoprazole by Using Piperidine

Ethanol (150 mL), DM water (50 mL) and Lansoprazole crude (10 gm) were taken in a reaction vessel at 30° C. and the contents were heated at a range of 40 to 45° C. Piperidine (1.0 gm) in DM water was added to the reaction mass at 40 to 45° C. till the pH of mass attained 8.3 to 8.8. The reaction mass was stirred at 40 to 45° C. to get a clear solution. Activated carbon was added to the clear solution at 40 to 45° C. and stirred. The reaction mass was filtered through hyflo and washed with ethanol. The reaction mass was cooled slowly to 5 to 10° C. and stirred for 1 hr. The material was filtered, washed with ethanol and dried under vacuum at 25 to 30° C. to get wet Lansoprazole (9 gm) HPLC Purity: >99.60%.

Wet cake of Lansoprazole was taken in acetone (200 mL) and heated at a range of 45 to 48° C. and stirred it till gets a clear solution. The solution was filtered through hyflo and washed with acetone. Isopropyl ether (400 mL) was added to clear solution at 40 to 45° C. till the haziness appeared. The reaction mass was cooled slowly to 5 to 10° C. and stirred. The material obtained was filtered and washed with isopropylether to get the wet Lansoprazole (5.5 gm), which is dried under vacuum at 40 to 50° C. to get the highly pure Lansoprazole (4.8 gm) HPLC Purity: >99.90%. The moisture content of the final product found to be 0.05%.

EXAMPLE (2)

Purification of Lansoprazole by Using Sodium 2-Ethyl Hexanoic Acid

Ethanol (600 mL) and Lansoprazole crude wet (60 gm) were taken in a reaction vessel at 25 to 30° C. and the contents heated at a range of 40 to 45° C. under stirring. A solution of sodium 2-ethylhexanoic acid (60 gm in ethanol 600 mL) was added to the reaction mass at 25 to 30° C. under stirring till the pH of reaction mass become 8.3 to 8.8. The reaction mass was stirred at 40 to 45° C. to get a clear solution, activated was added to the clear solution at 40 to 45° C. The reaction mass was filtered through hyflo and washed with ethanol at 40 to 45° C. The filtrate was cooled slowly to 0 to 5° C. and stirred the solid obtained was filtered, washed with chilled isopropyl ether and dried under vacuum at 25 to 30° C. to get the wet Lansoprazole (39 gm).

Wet cake of Lansoprazole was taken in acetone (840 mL) and heated at a range of 40 to 45° C. and stirred till it gets a clear solution, activated carbon was added to the clear solution. The solution was filtered through hyflo at 40 to 45° C. and washed with acetone. Isopropyl ether (1800 mL) was added to the clear solution at 40 to 45° C. till the haziness appeared. The reaction mass was cooled slowly to 5 to 10° C. and stirred for 1 hr. The solid obtained was filtered, washed with chilled isopropylether and dried under vacuum at 40 to 45° C. to get the highly pure Lansoprazole (24 gm.) HPLC Purity: >99.90%.

EXAMPLE (3)

Purification of Lansoprazole by Using Imidazole

Ethanol (600 mL) and Lansoprazole crude wet (60 gm) were taken in a reaction vessel at 25 to 30° C. and the contents heated at the range of 40 to 45° C. under stirring. A solution of imidazole (2.5 gm in ethanol 25 mL) was added to the reaction mass at 25 to 30° C. under stirring till the pH of reaction mass become 8.3 to 8.8. The reaction mass was stirred at 40 to 45° C. to get a clear solution, activated carbon was added to the clear solution at 40 to 45° C.; the reaction mass filtered through hyflo and washed with ethanol (10 mL). The filtrate was cooled slowly to 0 to 5° C. and stirred, the solid was filtered at 0 to 5° C. and washed with chilled isopropyl ether and dried under vacuum at 25 to 30° C. to get the wet Lansoprazole (47.5 gm).

Wet cake of Lansoprazole was taken in acetone (840 mL) and heated up to 40 to 45° C. and was stirred till it gets a clear solution, activated carbon was added to the clear solution and the reaction mass was stirred. The solution was filtered through hyflo at 40 to 45° C. and washed with acetone. Isopropyl ether (1800 mL) was added to the clear solution at 40 to 45° C. till the haziness appeared. The reaction mass was cooled slowly to 5 to 10° C. The solid obtained was filtered, washed with chilled isopropylether and dried under vacuum at 40 to 45° C. for 10 to 12 hrs to get the highly pure Lansoprazole (25 gm.) HPLC Purity: >99.90%.

We claim

1. An improved process for the purification of Lansoprazole of formula (I) in a solvent and in presence of an alkali salt of an organic acid or an organic base which is selected from a group consisting of piperidine and imidazole

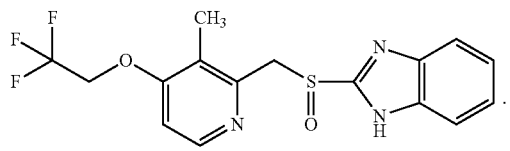

(I)

2. An improved process for the purification of Lansoprazole of formula (I) according to claim 1 comprising the steps of:
    a) dissolving crude Lansoprazole in a solvent in the presence of an alkali salt of an organic acid or an organic base selected from a group consisting of piperidine and imidazole; and
    b) isolating pure Lansoprazole.

3. A process according to claim 1, wherein the said solvent is selected from the group comprising of methanol, ethanol, n-propyl alcohol, isopropyl alcohol, n-butanol, isobutanol, tertiary butanol, water and mixtures thereof.

4. A process according to claim 3, wherein the solvent is aqueous ethanol.

5. A process according to claim 1, wherein the alkali salt of organic acid is selected from the group comprising of sodium 2-ethylhexanoate, potassium 2-ethylhexanoate, sodium acetate, potassium acetate, sodium citrate, and sodium lactate.

6. A process according to claim 5, wherein the alkali salt of organic acid is sodium 2-ethyl hexanoate.

7. A process according to claim 2, wherein the said purification is performed at a temperature in the range of −10° C. to 80° C.

8. A process according to claim 7, wherein the temperature range is 20° C. to 60° C.

9. A process according to claim 2, wherein the purity of Lansoprazole of formula (I) obtained is more than 99.0%.

10. A process according to claim 9, wherein the purity of Lansoprazole of formula (I) is greater than 99.90%.

* * * * *